(12) United States Patent
Shukla et al.

(10) Patent No.: US 10,058,506 B2
(45) Date of Patent: Aug. 28, 2018

(54) TUNABLE ANTI-MICROBIAL LOADED HYDROGELS

(71) Applicant: Brown University, Providence, RI (US)

(72) Inventors: Anita Shukla, Providence, RI (US); Shashank Shukla, Burlington, MA (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 14/942,435

(22) Filed: Nov. 16, 2015

(65) Prior Publication Data

US 2016/0136232 A1 May 19, 2016

Related U.S. Application Data

(60) Provisional application No. 62/080,218, filed on Nov. 14, 2014.

(51) Int. Cl.
| | |
|---|---|
| A61K 9/00 | (2006.01) |
| A61K 9/06 | (2006.01) |
| A61K 38/14 | (2006.01) |
| A61K 47/02 | (2006.01) |
| A61K 47/36 | (2006.01) |
| A61K 9/51 | (2006.01) |

(52) U.S. Cl.
CPC .............. *A61K 9/0014* (2013.01); *A61K 9/06* (2013.01); *A61K 38/14* (2013.01); *A61K 47/02* (2013.01); *A61K 47/36* (2013.01); *A61K 9/5115* (2013.01)

(58) Field of Classification Search
None
See application file for complete search history.

(56) References Cited

U.S. PATENT DOCUMENTS

| | | | | |
|---|---|---|---|---|
| 4,931,279 | A | 6/1990 | Bawa et al. | |
| 6,172,219 | B1 * | 1/2001 | Callegaro | A23L 3/3463 536/123.1 |
| 2003/0099682 | A1 * | 5/2003 | Moussy | A61B 5/0031 424/423 |
| 2006/0015083 | A1 * | 1/2006 | Munro | A61L 15/425 604/367 |
| 2013/0089599 | A1 * | 4/2013 | Desilva | A61K 9/51 424/450 |

FOREIGN PATENT DOCUMENTS

| | | |
|---|---|---|
| CN | 102228693 A | 11/2011 |
| EP | 0053936 A2 | 6/1982 |
| WO | 2005021057 A1 | 3/2005 |
| WO | 2009101518 A2 | 8/2009 |

OTHER PUBLICATIONS

Yadav S. et. al., Gellan-thioglycolic acid conjugate: Synthesis, characterization and evaluation as mucoadhesive polymer, Carbohydrate Polymers, 2014, 601-607, 99, Elsevier, India.

Yamamoto F. et. al., Acid gelation of gellan: Effect of final pH and heat treatment conditions, Carbohydrate Polymers, 2007, 517-527, 68, Elsevier, Brazil.

Zhao, Yu et. al., In situ cross-linked polysaccharide hydrogel as extracellular matrix mimics for antibiotics delivery, Carbohydrate Polymers, 2014, 63-69, vol. 105, Elsevier, Netherlands.

Agnihotri Sunil et. al., Controlled release of cephalexin through gellan gum beads: Effect of formulation parameters on entrapment efficiency, size, and drug release, European Journal of Pharmaceutics and Biopharmaceutics, 2006, 249-261, 63, Elsevier, India.

Ahmed Enas M., Hydrogel: Preparation, characterization, and applications: A review, Journal of Advanced Research, 2015, 105-121, vol. 6, Elsevier B.V., Netherlands.

Anand, Vikas et. al., Ion-exchange resins: carrying drug delivery forward, DDT, Sep. 2001, 905-914, vol. 6 No. 17, Elsevier, Netherlands.

Betz W. et. al., High Surface Area Graphitized Mesoporous Carbons, Sigma-Aldrich, United States.

Boateng, Joshua S. et. al., Wound Healing Dressings and Drug Delivery Systems: A Review, Journal of Pharmaceutical Sciences, Aug. 2008, 2892-2923, vol. 97, No. 8, Wiley InterScience (www.interscience.wiley.com).

Coutinho, Daniela F. et al., Modified Gellan Gum hydrogels with tunable physical and mechanical properties, Biomaterials, 2010, 7494-7502, vol. 31, Elsevier, Netherlands.

Coviello, Tommasina et. al., Polysaccharide hydrogels for modified release formulations, Journal of Controlled Release, 2007, 5-24, vol. 119, Elsevier, Netherlands.

D'Arrigo, Giorgia et. al., Gellan gum nanohydrogel containing anti-inflammatory and anti-cancer drugs: a multi-drug delivery system for a combination therapy in cancer treatment, European Journal of Pharmaceutics and Biopharmaceutics, 2014, 208-216, vol. 87, Elsevier, Netherlands.

Degim, Zelihagul et. al., Evaluation of chitosan gel containing liposome-loaded epidermal growth factor on burn wound healing, International Wound Journal, 2011, 343-354, Vo. 8, Blackwell Publishing Ltd, United States.

Drury, Jeanie L. et. al., Hydrogels for tissue engineering: scaffold design variables and applications, Biomaterials, 2003, 4337-4351, vol. 24, Elsevier, Netherlands.

(Continued)

*Primary Examiner* — Robert A Wax
*Assistant Examiner* — Quanglong N Truong
(74) *Attorney, Agent, or Firm* — Adler Pollock & Sheehan P.C.; Daniel J. Holmander, Esq.

(57) ABSTRACT

A tunable antimicrobial-loaded hydrogel formulation has a mechanical strength can be altered by changing the salt composition. The hydrogel formulation is preferably a Gellan film. The ion concentration in the gel material may be altered to obtain the desired gel strength. The hydrogel formulation is layered directly upon a skin area such as burnt skin. The hydrogel formulation includes a dosage of free antibiotic, such as the antibiotic is preferably vancomycin, for rapid release. The hydrogel formulation also includes microparticles and/or nanoparticles such as activated carbon powder that has adsorbed additional antibiotic. The particles are used to aid in attaining a timely or sustained release of the antibiotic drug.

18 Claims, 10 Drawing Sheets

(56) References Cited

OTHER PUBLICATIONS

Emeje, M.O. et al., Evaluation of the fluid uptake kinetics and drug release from gellan gum tablets containing metronidazole, International Journal of Biological Macromolecules 47 (2010) 158-163, Copyright 2010 Elsevier B.V.

Ferris, Cameron J. et. al., Modified gellan gum hydrogels for tissue engineering applications, Soft Matter, 2013, 3705-3711, vol. 9, RSCPublishing, United Kingdom.

Gong Y. et. al., An improved injectable polysaccharide hydrogel: modified gellan gum for long-term cartilage regeneration in vitro, Journal of Materials Chemistry, 2009, 1968-1977, 19, The Royal Society of Chemistry, Singapore.

Gulrez, Syed K. H. et. al., Hydrogels: Methods of Preparation, Characterisation and Applications, Progress in Molecular and Environmental Bioengineering—From Analysis and Modeling to Technology Applications, 2011, 117-151, InTech, Croatia.

Hameed, B.H. et. al., Adsorption of methylene blue onto bamboo-based activated carbon: Kinetics and equilibrium studies, Journal of Hazardous Materials, 2007, p. 819-p. 825, 141, Journal of Hazardous Materials, United States.

Hellriegel, Jan et al., A Biomimetic Gellan-Based Hydrogel as a Physicochemical Biofilm Model, Journal of Biomaterials and Nanobiotechnology, Apr. 2014, 83-97, 5, SciRes, United States.

Hsu B.B. et. al., Multilayer Films Assembled from Naturally-Derived Materials for Controlled Protein Release, Biomacromolecules, 2014, 2049-2057, 15, American Chemical Society, United States.

Jahromi S. H. et. al., Degradation of polysaccharide hydrogels seeded with bone marrow stromal cells, Journal of the Mechanical Behavior of Biomedical Materials, 2011, United Kingdom.

Jones, Annie et. al., Hydrogel dressings in the management of a variety of wound types: A review, Journal of Orthopaedic Nursing, 2005, S1-S11, Vol. 9 Suppl., Elsevier, Netherlands.

Kedzierewicz F. et. al., Effect of the formulation on the in-vitro release of propranolol from gellan beads, International Journal of Pharmaceutics, 1999, 129-136, 178, Elsevier, France.

Kelcogel Gellan Gum, Gellan Gum Book 5th Edition, 2007, 1-29, CP Kelco U.S., Inc., United States.

Kesavan K. et. al., Preparation and in vitro antibacterial evaluation of gatifloxacin mucoadhesive gellan system, Daru, 2010, 2370246, vol. 18, No. 4, India.

Lai, Cheng-Yu et al., A Mesoporous Silica Nanosphere-Based Carrier System with Chemically Removable CdS Nanoparticle Caps for Stimuli-Responsive Controlled Release of Neurotransmitters and Drug Molecules, JACS Articles, Mar. 20, 2003, p. 4451-p. 4459, American Chemical Society, United States.

Lee K.Y. et. al. Hydrogels for Tissue Engineering, Chemical Reviews, 2001, 1869-1880, vol. 101 No. 7, Amencan Chemical Society, United States.

Li B. et. al., Sustained release of vancomycin from polyurethane scaffolds inhibits infection of bone wounds in a rat femoral segmental defect model, Journal of Controlled Release, 2010, 221-230, 145, Elsevier, United States.

Lu H. et. al., Layer-by-layer self-assembly of minocycline-loaded chitosan/alginate multilayer on titanium substrates to inhibit biofilm formation, Journal of Dentistry, 2014, 1464-1472, 42, Elsevier, China.

Malmsten Martin, Antimicrobial and antiviral hydrogels, Soft Matter, Jun. 3, 2011, 8725-8736, 7, The Royal Society of Chemistry.

Matricardi, Pietro et. al., Preparation and Characterization of Novel Gellan Gum Hydrogels Suitable for Modified Drug Release, 2009, 3376-3391, vol. 14, Department of Drug Chemistry and Technologies, Faculty of Pharmacy, University of Rome "La Sapienza", Italy.

Miyazaki S. et. al., In situ-gelling gellan formulations as vehicles for oral drug delivery, Journal of Controlled Release, 1999, 287-295, 60, Elsevier, Japan, United Kingdom.

Mizrahi, Shimon et al., Osmotic dehydration phenomena in gel systems, Journal of Food Engineering, 2001, 87-96, vol. 49, Elsevier, Netherlands.

Moody Ann, Use of a hydrogel dressing for management of a painful leg ulcer, Wound Care, Jun. 2006, S12-S17.

Morris Edwin R. et. al., Gelation of gellan—A review, Food Hydrocolloids, 2012, 373-411, vol. 28, Elsevier, Netherlands.

Narkar M. et. al., Stomach-Specific Controlled Release Gellan Beads of Acid-Soluble Drug Prepared by Ionotropic Gelation Method, AAPS PharmSciTech, Mar. 2010, 267-277, vol. 11 No. 1, American Association of Pharmaceutical Scientists, United States.

Newcombe, Gayle et al., Granular activated carbon: importance of surface properties in the adsorption of naturally occurring organics, Colloids and Surfaces A: Physicochemical and Engineering Aspects, 78 (1993) 65-71; Copyright 1993 Elsevier Science Publishers B.V.

Novac O. et. al., Antibacterial quaternized gellan gum based particles for controlled release of ciprofloxacin with potential dermal applications, Materials Science and Engineering, 2014, 291-299, C 35, Elsevier, Romania.

Oliveira, J.T. et. al., Gellan gum: A new biomaterial for cartilage tissue engineering applications, Journal of Biomedical Materials Research Part A, Aug. 5, 2009, 852-863, Wiley Periodicals, Inc., United States.

Picone Carolina S.F. et. al., Influence of pH on formation and properties of gellan gels, Carbohydrate Polymers, 2011, 662-668, 84, Elsevier, Brazil.

Ribeiro Pereira, Diana et. al., Development of Gellan Gum-Based Microparticles/Hydrogel Matrices for Application in the Intervertebral Disc Regeneration, Tissue Engineering: Part C, 2011, 961-975, vol. 17, Mary Ann Liebert, Inc., United States.

Shukla A. et. al., Design of multi-drug release coatings targeting infection and inflammation, Journal of Controlled Release, 2011, 159-166, 155, Elsevier, United States.

Shukla A. et. al., Release of vancomycin from multilayer coated absorbent gelatin sponges, Journal of Controlled Release, 2012, 64-71, 157, Elsevier, United States.

Shukla A. et. al., Tunable Vancomycin Releasing Surfaces for Biomedical Applications, small, 2010, 2392-2404, vol. 6, No. 21, Wiley-VCH Verlag GmbH & Co. KGaA, Weinheim, Germany.

Siddiqui, Farah et. al., Gellan-Based Systems for Sustained Ophthalmic Delivery of Ofloxacin, Continental J. Pharmaceutical Sciences, 2008, 1-14, vol. 2, Wilolud Online Journals, United States.

Soft Matter, Mechanics and physics of hydrogels, Soft Matter, 2012, 8006-8007, vol. 8, The Royal Society of Chemistry.

Stammen Jason A. et. al., Mechanical properties of a novel PVA hydrogel in shear and unconfined compression, Biomaterials, 2001, 799-806, vol. 22, Elsevier, Netherlands.

Sun, Guoming et. al., Dextran hydrogel scaffolds enhance angiogenic responses and promote complete skin regeneration during burn wound healing, PNAS, Dec. 27, 2011, 20976-20981, vol. 108, No. 52, PNAS, United States.

Uhrich K.E. et. al., Polymeric Systems for Controlled Drug Release, Chemical Reviews, 1999, 3181-3198, 99, American Chemical Society, United States.

Verma A. et. al., Rifabutin-loaded Floating Gellan Gum Beads: Effect of Calcium and Polymer Concentration on Incorporation Efficiency and Drug Release, Tropical Journal of Pharmaceutical Research, 2011, 61-67, 10 (1), Pharmacotherapy Group, Faculty of Pharmacy, University of Benin, Nigeria.

Veyries M.L. et. al., Controlled release of vancomycin from Poloxamer 407 gels, International Journal of Pharmaceutics, 1999, 183-193, 192, Elsevier, France.

Wu, Peng et. al., Drug/device combinations for local drug therapies and infection prophylaxis, Biomaterials, 2006, 2450-2467, 27, Elsevier, Netherlands.

Xing, Bengang et. al., Hydrophobic Interaction and Hydrogen Bonding Cooperatively Confer a Vancomycin Hydrogel: A Potential Candidate for Biomaterials, J. Am. Chem. Soc. 2002, 14846-14847, vol. 124, American Chemical Society, United States.

* cited by examiner

| | GELLAN | GELLAN+VANCOMYCIN (*) | GELLAN+VANCOMYCIN+ VANCOMYCIN LOADED NANOCARBONS(*) |
|---|---|---|---|
| SHEET+ ENGINEERING YOUNG'S MODULUS (Pa) | $1.66 \times 10^5 \pm 6.36 \times 10^4$ | $1.35 \times 10^5 \pm 4.67 \times 10^4$ | $6.89 \times 10^5 \pm 2.44 \times 10^4$ |
| AMORPHOUS+ DYNAMIC YOUNG'S MODULUS (Pa) | GELLAN(#) | GELLAN+VANCOMYCIN (@) | GELLAN+VANCOMYCIN+ VANCOMYCIN LOADED NANOCARBONS (#,@) |
| | $13.34 \pm 5.96$ | $11.45 \pm 5.98$ | $29.71 \pm 6.26$ |

NOTE (USING ONE-WAY AND TWO-WAY ANOVA):
+ SIGNIFICANCE BETWEEN SHEET AND AMORPHOUS FOR EACH GEL TYPE: $p < 0.001$, $n = 3$
* SIGNIFICANCE BETWEEN SHEET GELLAN AND SHEET COMPOSITE GELS: $p < 0.05$; $n = 3$
SIGNIFICANCE BETWEEN AMORPHOUS GELLAN AND AMORPHOUS COMPOSITE GELS: $p < 0.05$; $n = 3$
@ SIGNIFICANCE BETWEEN AMORPHOUS GELLAN AND VANCOMYCIN AND AMORPHOUS COMPOSITE GELS: $p < 0.05$, $n = 3$

FIG. 6

KEY - A: AMORPHOUS; S: SHEET; -: NEGATIVE CONTROL BLANK DISC; +: POSITIVE VANCOMYCIN SensiDisc(R).
(A) NO ZONE OF INHIBITION IS NOTED FOR S. aureus 25923 AGAINST EMPTY GELLAN HYDROGEL SAMPLES.
(B) A CLEAR ZONE OF INHIBITION IS VISIBLE IN BOTH AMORPHOUS AND SHEET HYDROGEL SAMPLES AGAINST S. aureus.
(C) NO ZONE OF INHIBITION IS NOTED FOR EMPTY GELLAN HYDROGELS AGAINST MRSA MW2.
(D) A CLEAR ZONE OF INHIBITION IS VISIBLE IN BOTH AMORPHOUS AND SHEET HYDROGEL SAMPLES AGAINST MRSA MW2.

TUNABLE ANTI-MICROBIAL LOADED HYDROGELS

CROSS-REFERENCE TO RELATED APPLICATION

This application claims priority to U.S. Provisional Patent Application No. 62/080,218 filed Nov. 14, 2014, which is incorporated herein by reference.

BACKGROUND OF THE INVENTION

1. Field of the Invention

The subject disclosure relates to tunable antimicrobial-loaded polymer base formulations having a two-part, rapid and sustained, delivery of a drug.

2. Background of the Related Art

In the United States, there are millions of infections per year from resistant bacteria. Some of these infections even result in death. The monetary costs associated with these infections are billions of dollars, not to mention the burden of the actual infections themselves. In burn victims, wound infection is particularly troublesome as it is the leading cause of death in ICUs for burn victims, in the United States. Some of the bacterial or fungal pathogens are *Staphylococcus aureus*, methicillin-resistant *Staphylococcus aureus* (MRSA) and *Candida albicans*.

Current treatments are usually some combination of sterile gauze, systemic drug administration, and hydrogels to promote wound healing, provide moisture, and soothe the wound. For example, see U.S. Pat. No. 4,931,279 to Bawa et al. However promising, these treatments have limitations. One such treatment is silver sulfadiazine, which is often the active antimicrobial agent in existing topical therapies. Silver sulfadiazine has high toxicity for keratinocytes and fibroblasts, key wound healing cells, thus preventing optimal wound healing. Silver sulfadiazine must also be applied several times per day.

SUMMARY OF THE INVENTION

In view of the above, a need exists for a wound treatment that would effectively inhibit bacterial infection growth, promote wound healing, prevent repeated daily application, not require systemic delivery, and/or have tunable delivery. The subject technology addresses all of these needs by providing polymer base formulations that provide a topical drug delivery system with tunable release and mechanical properties. As a result of the topical delivery, off-site toxicity and bacterial resistance are limited or prevented. Preferably, the treatment delivers small molecules including antibiotics.

A preferred polymer base forms a hydrogel such as Gellan gum. The hydrogel formulation may be ointment, semi-crystalline, or a sheet. The hydrogel formulation may quickly release a free form of the drug as well as release a drug contained therein over a period of hours or days. The subsequent sustained release reduces the need for reapplication, which enhances patient compliance as patients often suffer pain and inconvenience in changing bandages.

Gellan gum, a natural anionic heteropolysaccharide, provides strength and versatility. Along with high ion concentration, Gellan gum improves the strength of the hydrogel formulation. Gellan gum also improves long term drug release. One version of the Gellan gum varies from ointment to sheet form, without the need for covalent or harsh chemical crosslinking modifications.

Preferably, the hydrogel formulation can fit a variety of wound configurations. By using a hydrogel formulation, the high water content enhances tissue repair by promoting cell viability and autolytic debridement. Further, the hydrogel formulation can fill in dead space and prevent excessive dosing by providing slow sustained release.

In one embodiment, the subject technology is directed towards tunable antimicrobial-loaded hydrogel formulations. In one embodiment, the subject technology is a hydrogel formulation, where the pH level can be altered by changing the salt composition. The hydrogel formulation is preferably a Gellan film. In one method, the hydrogel formulation is layered directly upon a skin area such as burnt skin. The hydrogel formulation includes any dosage of antibiotic. One preferred antibiotic is vancomycin. The hydrogel formulation can also include microparticles and/or nanoparticles that are preferably selected from an ion exchange resin, activated carbon powder, or a combination of the two. The particles are used to aid in attaining a timely or sustained release of the antibiotic drug. The polymer and ion concentration in the gel material may be altered to obtain the desired gel strength.

It should be appreciated that the subject technology can be implemented and utilized in numerous ways, including without limitation as a process, an apparatus, a system, a device, and a method for applications now known and later developed. These and other unique features of the system disclosed herein will become more readily apparent from the following description and the accompanying drawings.

BRIEF DESCRIPTION OF THE DRAWINGS

So that those having ordinary skill in the art to which the disclosed system appertains will more readily understand how to make and use the same, reference may be had to the following drawings.

DETAILED DESCRIPTION OF PREFERRED EMBODIMENTS

The subject technology overcomes many of the prior art problems associated with treating wounds. The advantages, and other features of the system disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

Hydrogels are three-dimensional, water-swollen structures comprised of hydrophilic cross-linked networks. Hydrogels range from ointment, to semi-crystalline, to sheet structures. Hydrogels are diluted cross-linked systems, demonstrating no flow at steady state and are capable of absorbing large amounts of water. For wounds, hydrogels are desirable because hydrogels create a moist healing environment and prevent adherence to wounds because of low interfacial tension. Hydrogels have a polymer base such as Gellan gum, alginate, and/or pectin. The following discussion relates to Gellan gum for simplicity but as noted other bases now known and later developed may be utilized. The chemical structure of Gellan gum is below.

The strength and release properties of hydrogels is a function of pH, Gellan concentration, and ion concentration. Table 1 below illustrates a table for ointment and sheet formulations of hydrogels. As a sheet, the hydrogel may be formed or cut into any desired shape, applied to a wound, and held in place with a dressing such as sterile gauze. The ointment hydrogel can be extruded from a needle (e.g., 3 mL 25.5 gauge) directly onto a site.

TABLE 1

| TYPE | ION CONCENTRATION (mM $CaCl_2$) | GEL CONCENTRATION | pH |
| --- | --- | --- | --- |
| OINTMENT | 1 | 1 | 5.5 7.4 |
| SHEET | 7 | 4 | |

Figure 1:
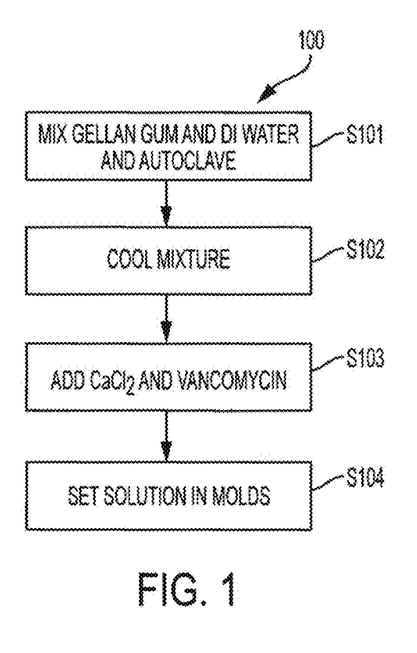
FIG. 1 illustrates a method of forming a hydrogel in accordance with the subject disclosure.

Referring now to FIG. 1, a method 100 of forming a hydrogel in sheet form is shown. At step S101, Gellan gum and deionized water are mixed together and autoclaved from 15 to 45 minutes at 121° C. or until the Gellan gum is dissolved in the deionized water. Step S102 is a cooling step in order to prevent exposing the drug additive to high temperature. A typical cooling time is 30 seconds. At step S103, a solution of $CaCl_2$ is added and mixed thoroughly to increase the ion concentration. The solution of $CaCl_2$ also includes a drug such as vancomycin. Vancomycin is preferred because vancomycin is highly effective against several Gram-positive bacteria with a relatively low minimum inhibitory concentration (MIC).

At step S104, the solution is poured into the desired molds and allowed to set at room temperature. An ointment or semi-crystalline hydrogel is formed in a similar manner. As would be understood by one of ordinary skill in the art, a hydrogel produced in accordance with the method 100 would provide ample free vancomycin for quick release. However, an alternative hydrogel that provides a sustained release over a multi-day period would also be beneficial. To obtain a more tunable and long-term release, vancomycin can be incorporated into nanoparticles for subsequent incorporation into the hydrogel.

For example, ion exchange resins can be used to reverse ion exchange, mix the drug in ionic form to form resinate, release in conditions with a counter ion, and load a drug (e.g., vancomycin) at a high pH and release at a low pH. In one embodiment, the nanoparticles are activated carbon with an average diameter of 35 nm possessing a pentagonal configuration and forming aggregates to the 400 nm range. The carbon nanoparticles are structurally homogenous with graphite-like domains, low functional groups, and low occurrences of imperfections. Typical generation is from pure charcoal through carbonization and activation processes. Such resulting micro-, meso-, and macro-pores are able to adsorb many different size molecules within the pores for subsequent release under appropriate conditions. As the activated carbon turns the resulting hydrogel formation black, such hydrogel formations are easily recognized.

In one embodiment, a hydrogel formation in a sheet form provides drug release over a nine day period. Several formulations are possible including the following: Gellan gum, free vancomycin, and vancomycin loaded NC; Gellan gum, free vancomycin, and vancomycin loaded ion-exchange resins; and Gellan gum, free vancomycin, vancomycin loaded NC, and vancomycin loaded ion-exchange resins. The hydrogel formation may be in an ointment form to provide extended drug release.

Table 2 below illustrates several possible compositions for ointment and sheet formulations of hydrogels.

TABLE 2

| Form | Sample Type | Gellan concentration (% w/v) | $CaCl_2$ concentration (mM) | Free vancomycin concentration (% w/v) | Carbon concentration (% w/v) | Total vancomycin (% w/v) |
| --- | --- | --- | --- | --- | --- | --- |
| Ointment | Gellan | 1 | 1 | 0 | 0 | 0 |
| Ointment | Gellan + vancomycin | 1 | 1 | 0.06 | 0 | 0.06 |
| Ointment | Gellan + vancomycin + vancomycin loaded carbons | 1 | 1 | 0.06 | 0.04 | 0.06 |
| Sheet | Gellan | 4 | 7 | 0 | 0 | 0 |
| Sheet | Gellan + vancomycin | 4 | 7 | 0.06 | 0 | 0.06 |
| Sheet | Gellan + vancomycin + vancomycin loaded carbons | 4 | 7 | 0.06 | 0.04 | 0.06 |

Figure 2:
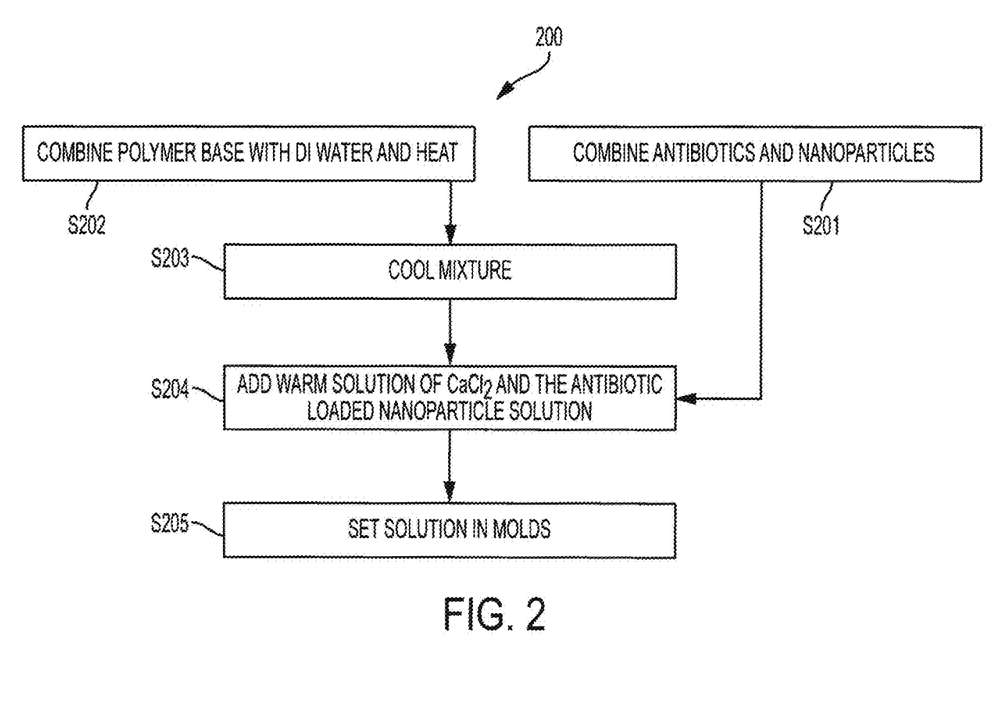
FIG. 2 illustrates another method of forming a hydrogel in accordance with the subject disclosure.

Referring now to FIG. 2, another method 200 of forming a hydrogel in sheet form is shown. At step S201, vancomycin and carbon nanopowder are combined. The vancomycin and carbon nanopowder may be combined by placement in a container that is agitated for a period of time. The agitation may be for just 10 minutes, hours, a day, or even days. Activated carbon is highly porous. In other words, the carbon particles have branching inner passages into which gases and/or chemicals enter. The agitation over an extended period facilitates entry of the vancomycin effectively into the inner passages. In one embodiment, the nanopowder activated carbon has a typical diameter of 500 nm with a typical pore diameter of 13.7 nm.

At step S202, Gellan powder and deionized water are combined and autoclaved. For example, the materials are heated to 120 degrees C. for 15 to 45 minutes until a homogenous state is reached. At step S203, the combination of Gellan powder and water are cooled. For example, the cooling can be at room temperature for 30 seconds. At step S204, the cooling Gellan powder and water are combined with a warm solution of $CaCl_2$, free vancomycin and the agitated vancomycin loaded carbon nanopowder particle solution. The $CaCl_2$ provides $Ca^{2+}$ ions that facilitate gelation. The mixture is stirred with a glass rod to obtain even distribution.

High Gellan gum and ion concentration improves gel strength. The activated carbon increases the amount of vancomycin loaded in the hydrogel, which is then subsequently released over an extended duration. The resulting hydrogel formulation can take the form of an ointment or a sheet for placement directly on a wounded area. A sheet form may include 4% w/v Gellan, 7 mM $CaCl_2$, and 0.6 mg/mL vancomycin. An ointment form may include 1% w/v Gellan, 1 mM $CaCl_2$, and 0.6 mg/mL vancomycin. Strength of the hydrogel formulation is a function of ion concentration (e.g., $CaCl_2$) and gel concentration. At step 205, the mixture is poured into molds for setting in sheet form or put in a container for the ointment form.

Figure 3:
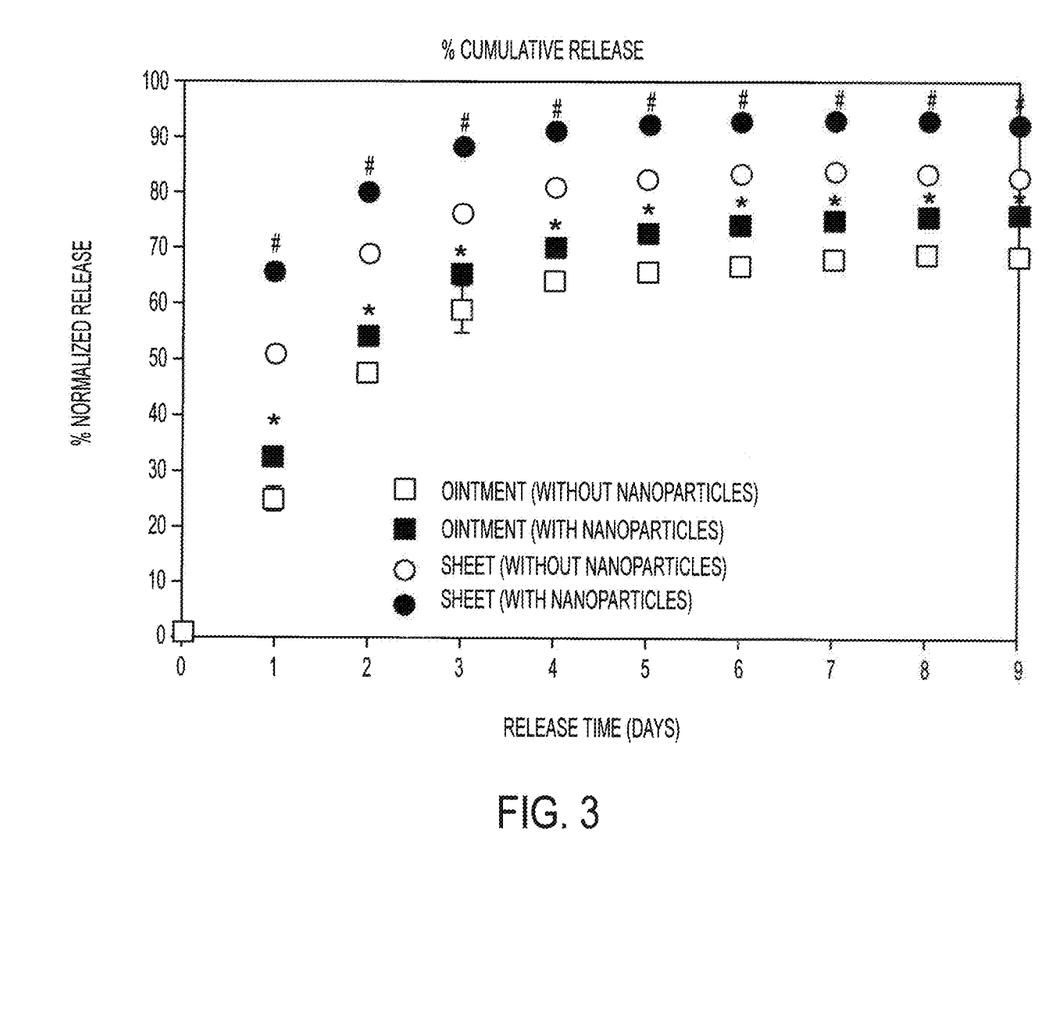
FIG. 3 illustrates release profiles of free vancomycin and vancomycin loaded carbon nanopowder particles loaded within hydrogels constructed in accordance with the subject technology.

Generally, drug release is directly proportional to drug concentration. However, by including free vancomycin and vancomycin loaded in carbon nanoparticles, a sustained release of vancomycin follows the rapid release that occurs initially. FIG. 3 illustrates two release profiles of Gellan hydrogels. One of the release profiles outlines free vancomycin release from the hydrogels and the other outlines release from vancomycin loaded carbon nanopowder particles incorporated within gellan hydrogels. As can be seen, the dual release will allow for infrequent bandage changes and application, which will facilitate patient compliance. Without being limited to any particular theory, the slow release is due to the highly porous nanoparticle with different types of pores. Once adsorbed, the vancomycin has to navigate through the tortuous path of the nanoparticle pores, through the Gellan crosslinks, and into the surrounding environment whereas the free vancomycin only has to navigate through the hydrogel.

Figure 4:
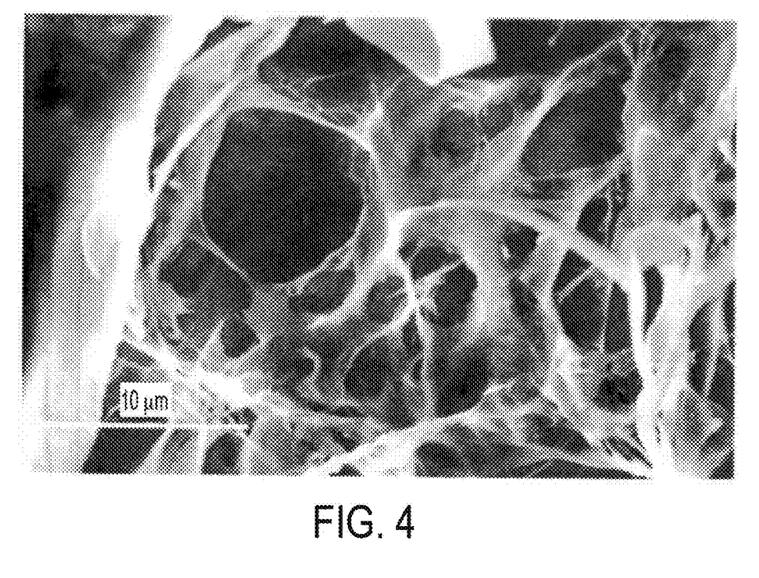
FIG. 4 is a scanning electron microscopy (SEM) cross-sectional image of a freeze-dried sheet hydrogel in accordance with the subject disclosure.

FIG. 4 is a scanning electron microscopy (SEM) image taken of a sheet hydrogel sample to visualize the microstructure using a fully automated LEO 1530 VP ultra-high resolution field emitter SEM at 10 kV at ultra high vacuum. The hydrogel sample was freeze-dried in liquid nitrogen and fractured prior to placing it in the SEM vacuum chamber.

Figure 5:
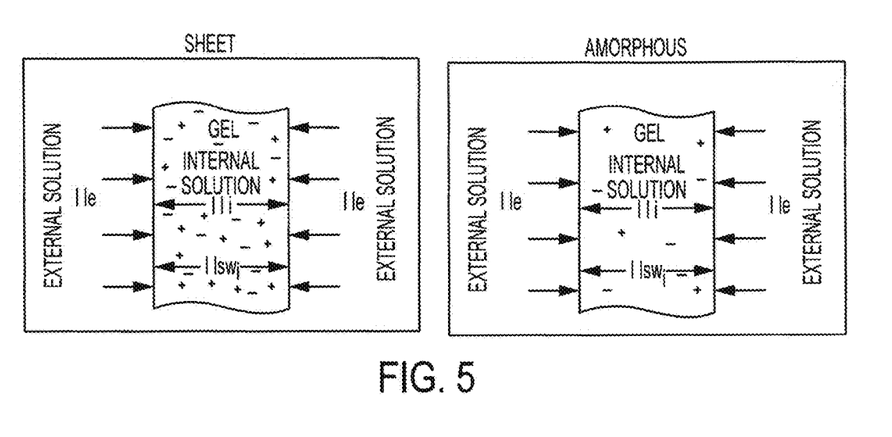
FIG. 5 illustrates how release kinetics are influenced by swelling-based diffusion for hydrogels in accordance with the subject disclosure.

In comparing sheet hydrogels to ointment hydrogels, it is envisioned that the hydrogels would provide greater cumulative release as a result of swelling-based diffusion. Swelling-based diffusion depends upon polymer concentration, ion concentration, solvent ion concentration, and osmotic pressure. Since the sheet form has a higher concentration of polymer and ions, a relatively higher concentration of counterions is present, which leads to a larger osmotic pressure difference. The osmotic pressure difference leads to greater swelling of the sheet hydrogel. This higher uptake of water causes a more rapid drug release as illustrated in FIG. 5.

Figure 6:
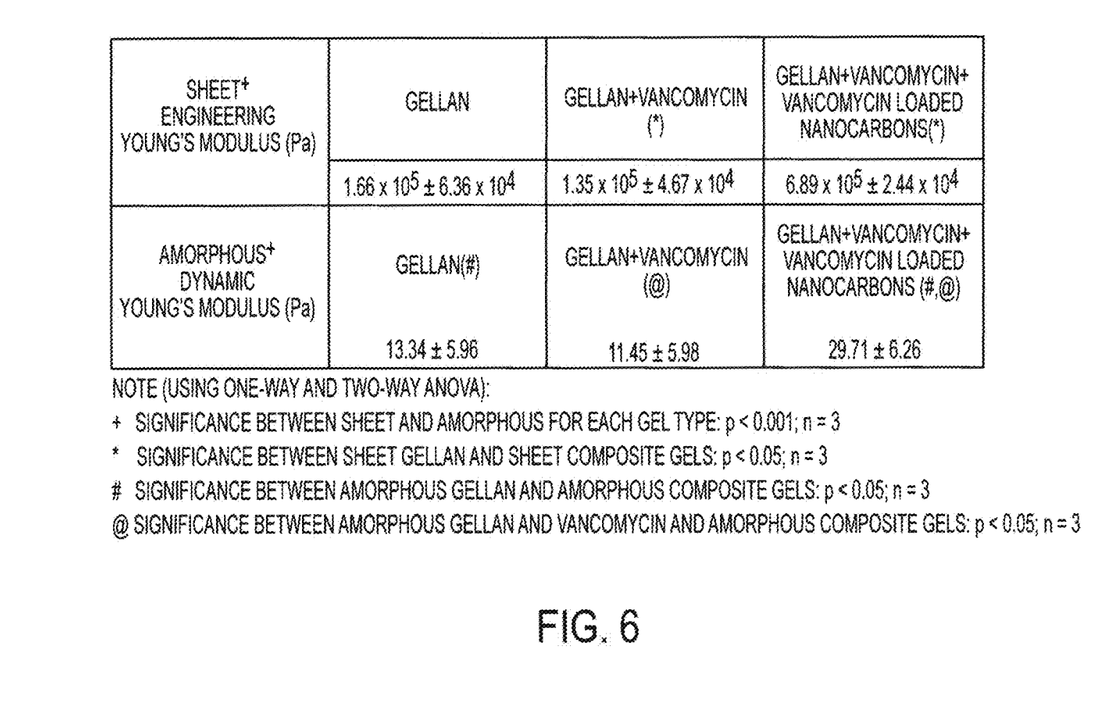
FIG. 6 is a table summarizing the mechanical properties of hydrogels in accordance with the subject technology.

Referring now to FIG. 6, a table summarizes the mechanical properties of hydrogels in accordance with the subject technology. The different symbols indicate significance between the corresponding samples. In order to optimize performance of the hydrogel formulation, one should consider the following properties: compression; shear stress; Young's modulus; and linear viscoelastic measurement. The hydrogel formulation can further be characterized in terms of physical properties such as mesh size, visual appearance, and in vitro degradation. In vitro drug release analysis has demonstrated the effectiveness of hydrogels in accordance with the subject technology.

The sheet hydrogel mechanical properties were evaluated using a Bose Enduratec® ELF 3200 compression instrument. The initial gel height (W) was measured and gel base was moved closer to the indenter. The indenter was manually moved down until contact (spike in load). The initial displacement at contact was recorded (X). The indenter was manually moved down until 0.5 g constant load was achieved and the displacement at 0.5 g load was recorded (Y). Distance traveled (Z) was calculated by subtracting Y from X. Z was subtracted from W to obtain actual test height (AW). 10% of AW was used as a compressive strain ($\epsilon$) boundary and compressive load ($\sigma$) was recorded. Engineering Young's moduli (E) was determined by using the slope of the linear portion of the graph, i.e., $E=\sigma/\epsilon$.

As it is impractical to perform compression analysis on ointment samples, we utilized rheometry to determine the mechanical properties, as has been done previously. A TA Advanced Rheometer 2000 was used to evaluate the dynamic Young's moduli. Briefly, ointment hydrogel samples were poured into the surface of the instrument, taking care as to not over/under flow the volume. The upper plate was lowered to the contact height of the ointment hydrogel and rotated manually to ensure complete contact. Using a 3% strain, a frequency sweep was run starting at 1 rad/s angular frequency and ramping to 50 rad/s. Using the software provided with the instrument, dynamic Young's moduli were calculated.

As shown in FIG. 6, the Young's moduli values of all three types of sheet hydrogels are significantly higher (indicated by the +) than the ointment hydrogels (order of magnitude $10^5$ vs. $10^1$). This difference demonstrates the mechanical tenability of the hydrogels ranging from very low mechanical strength in ointment form to several orders of magnitude higher in sheet form. Changes in polymer and ion concentration contributed to the vast difference in mechanical strength as ointment hydrogels are weaker than sheet hydrogels due to fewer polymer crosslinks and lower amount of counterions to preserve the helical structure.

There is also significant differences in Young's moduli between empty, vancomycin loaded, and nanoparticle loaded hydrogels (indicated by *, #, @). For both ointment and sheet, the carbon nanopowder particles significantly increase the mechanical strength, which can be attributed to their size and reinforcement of the polymer crosslinks. These carbon nanoparticles, particularly when aggregated, embed between the microporous structure of the hydrogel, increasing mechanical stability. In contrast, vancomycin does not play a role in affecting Young's moduli values due to its significantly smaller size.

Figure 7:
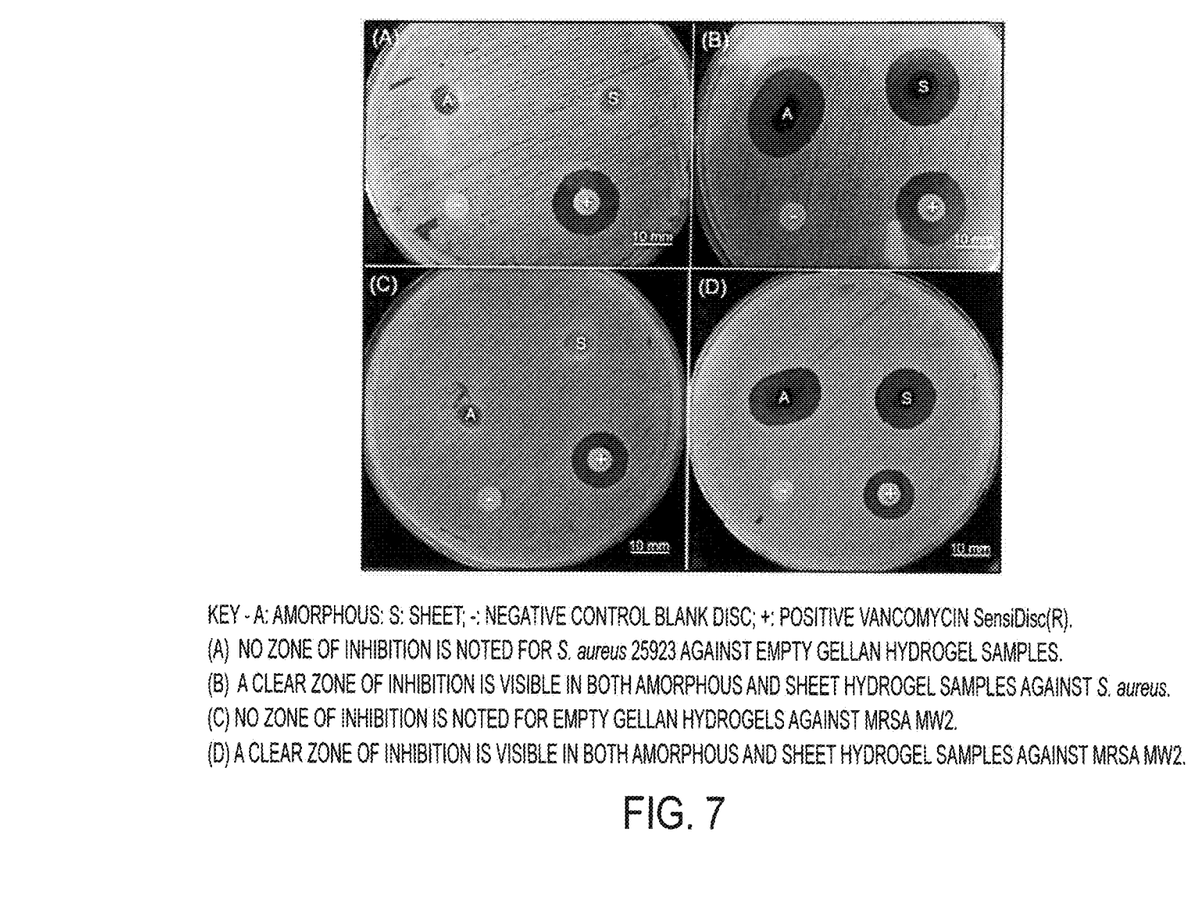
FIG. 7 illustrates a modified agar plate assay of hydrogels in accordance with the subject technology.

Referring now to FIG. 7, a modified agar plate assay of hydrogels in accordance with the subject technology is shown. Inhibition of *S. aureus* 25923 and MRSA MW2 growth by the hydrogels and the hydrogel release samples was determined using a modified agar plate assay, microdilution assay, and bacteria solution clearance assay. *S. aureus* and MRSA were chosen due to their prevalence in burn wound infection and recommendation by the Clinical and Laboratory Standards Institute (CLSI).

For the modified agar plate assays, agar plates were formulated using Bacto™ agar and CMHB. The plates were then coated evenly with *S. aureus* or MRSA at a concentration of $10^8$ CFU/mL for 16-18 hours, ensuring that the bacteria are in their exponential growth phase. After coating the agar with bacteria, hydrogels loaded with vancomycin and vancomycin-loaded activated carbon were placed on the plates along with unloaded gellan hydrogels as negative controls and 30 ug vancomycin susceptibility discs as positive controls. Following 18 hours of incubation at 37° C., agar plates were imaged and the zones of inhibition were measured with successful results.

Figure 8:
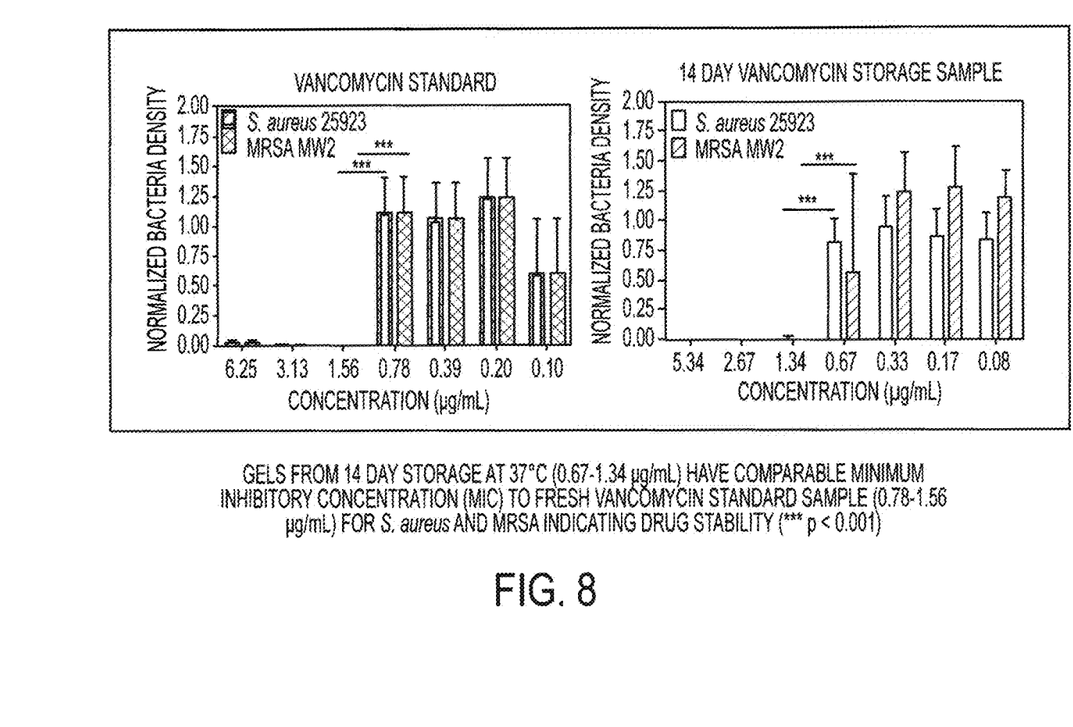
FIG. 8 illustrates a microdilution assay of hydrogels in accordance with the subject technology.

Referring now to FIG. 8, a microdilution assay of hydrogels in accordance with the subject technology is shown. Frozen release samples were added to 96 well clear bottom plates. The release samples were sterile filtered and added in triplicate and diluted with an equal volume of 2×CMHB, resulting in a final concentration of 1×CMHB. The samples were then serially diluted in 1×CMHB. As a control, sterile 0.01 M PBS without any vancomycin was also diluted. S. aureus was isolated and added to the diluted release samples at a final concentration of $10^5$ CFU/mL, along with the positive controls of PBS. Negative controls of PBS did not contain any bacteria. Controls of fresh, non-hydrogel incorporated vancomycin with a known concentration were used as well. The plates were incubated at 37° C. for 18 hours with low agitation. After incubation, the optical density (OD) of all the wells in the plates was measured at 600 nm using a Cytation3 plate reader. The normalized bacteria density was calculated, wherein the normalized bacteria density is equal to the ($OD_{600,\ sample}$ minus $OD_{600,\ negative\ control}$) divided by ($OD_{600,\ positive\ control}$ minus $OD_{600,\ negative\ control}$).

The results of bacterial solution clearance assays were also successful. For bacteria solution clearance assays, 5 mL of S. aureus at a concentration of $10^6$ CFU/mL was added to a 15 mL test tube. Hydrogel samples with carbons, positive vancomycin SensiDiscs™, and empty negative control samples were submerged directly in the bacteria solution. After three and 11 days, 1 mL of the solution was removed and remaining CFU/mL was measured in a cuvette at 600 nm using a Spectronic 200® Spectrophotometer. 1 mL of fresh 1×CMHB was added to the test tubes to keep the volume consistent. Digital images of the solutions were also obtained at each time point. All of the bacteria experiments were repeated with MRSA at the same concentrations and OD measured at 600 nm to evaluate the hydrogel efficacy against resistant strains.

Figure 9:
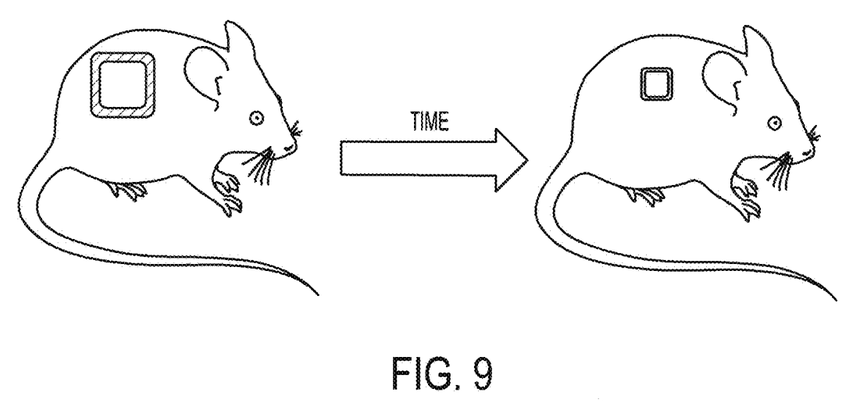
FIG. 9 illustrates in vivo mouse experiments in accordance with the subject technology.

Referring to FIG. 9, in vivo hydrogel antibacterial efficacy was also proven. FIG. 9 illustrates in vivo mouse experiments in accordance with the subject technology. In order to test the hydrogel efficacy, a bacteria concentration that is able to provide 100% death of the animal within 7 days of infection is needed. Briefly, mice are anesthetized via intraperitoneal injection and a burn is applied to the dorsal side of mice, using a heated brass block directly applied against exposed skin. The wound is infected with bacteria including S. aureus 25923 or MRSA MW2 strains of bacteria at $1\times10^8$ cells/mouse, $1\times10^9$ cells/mouse, or $1\times10^{10}$ cells/mouse. Animals are monitored to evaluate at what concentration death is achieved within 7 days. Painkillers (Buprenorphine) are also provided to the animals subcutaneously at a concentration of 1 mg/kg.

Topical treatment is initiated after 24 hours of applying the burn infections to evaluate the effect of topical hydrogel dressings on animal survival. Treatment is provided and animals were followed for a 7 day period. At the conclusion of the experiments, live animals will be euthanized via $CO_2$ inhalation and cervical dislocation. Treatment conditions include: saline, empty hydrogels, vancomycin, vancomycin hydrogels, and vancomycin hydrogels with vancomycin loaded carbon nanopowders. Both ointment and sheet hydrogels will be evaluated.

Animals were anesthetized with ketamine-xylazine (90-100 mg/kg ketamine and 510 mg/kg xylazine) intraperitoneal injection and infection is applied by adding predetermined concentrations of bacteria in a solution using a needle. Wound size is evaluated immediately after burn application and again at the conclusion of the experiment using calipers to measure any changes in wound site post hydrogel application. Proper painkillers according to the IACUC protocols are administered throughout the course of the experiment.

The bacterial burden within blood was evaluated. At day 5, animals are anesthetized with ketamine-xylazine and the thoracic cavity is opened to expose the heart. Approximately 1 mL of blood via cardiac puncture is collected and interrogated for bacteria colony forming unit (CFU) content. Subsequently the liver, lung, spleen, kidneys, and brain are harvested; the tissue is then disrupted and the material is tested to determine the number of colony forming units within the tissues.

Figure 10:
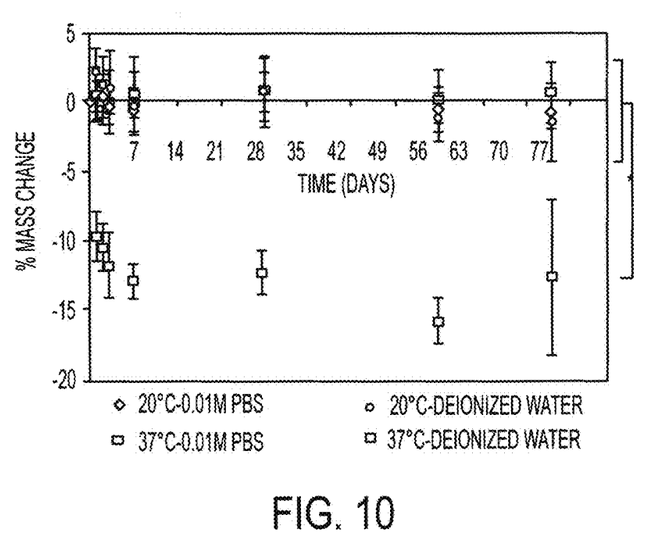
FIG. 10 illustrates long-term in vitro water uptake of hydrogels in accordance with the subject technology.

Hydrogels in accordance with the subject technology uptake water over time as shown in FIG. 10. Hydrogel mass was evaluated by assessing the percent mass change over 74 days of sheet hydrogel samples in two different solutions: 0.01 M PBS and deionized water. The samples were also placed in two different temperatures: room temperature (20° C.) and physiological temperature (37° C.). No significant mass change was noticed in all of the samples except those stored at 37° C. in deionized water. There was 12.5±5.6% mass change over 74 days in these samples, indicating that the hydrogel undergoes some degradation. The degradation can be attributed to the lack of ions in the deionized water, leading to an ion diffusion gradient out of the hydrogel therefore instability due to breaking of polymer crosslinks.

Burn wound infections seen clinically can easily become infected with resistant and non-resistant strains of S. aureus. By using a hydrogel system in accordance with the subject technology, one is able to combat both of the strain type to effectively eradicate and prevent future infections. By utilizing inexpensive, FDA approved, biocompatible, and easily available and modifiable materials, the instant wound dressings have an easier path to translation and FDA approval. Recurring burn infections are debilitating due to the weakened immune system. By providing a therapy that prevents bacteria growth recurrence, chances for subsequent infection onset are greatly reduced.

The time release of small molecule antibiotics such as vancomycin from hydrogel systems is tunable. One timescale is 0-48 hours. By controlling the time release of vancomycin, gellan hydrogel systems are a more long-term treatment option. Through using vancomycin, other Gram-positive bacteria infections are treatable as well.

Several studies have been conducted relating patient compliance to pain associated with frequent dressing changes. Patients are therefore more reluctant to adopt a therapy where daily reapplication is required, because of the severe pain associated with dressing removal and adherence. Although the rapid release over 24 hours is able to eradicate bacteria growth, it is the sustained release above effective concentration that prevents daily reapplication of wound dressings. This is in agreement with past studies that have been done to show the need for a high concentration of antibiotics to completely eradicate bacteria growth. Currently, vancomycin is often provided through intravenous (IV) injections, requiring a hospital stay and increasing care costs. Hence, there is a potential savings to hospital care cost because the hydrogel dressing can be provided in the clinic or with outpatient care.

Due to the patient-specific tunability of the hydrogels of the subject technology, patients and clinicians alike will likely be more willing to use the dressings compared to those that require frequent reapplication. The simplicity of the composition is highly desirable in terms of clinical translation of the wound dressing. Hydrogels in accordance with the subject technology may also include one or more additional compounds such as antibiotics (e.g., gentamicin, clindamycin and the like), antifungal compounds, anti-inflammatory compounds, proteins (e.g., growth factors) and enzymes to promote wound healing, hemostatic agents, diagnostic and contrast agents, extracellular matrix components, and combinations thereof.

The subject technology is useful for treatment of wounds such as ulcers, burns and the like. A bandage can be used over the hydrogels for holding the hydrogels in place at the wound site. The subject technology is particularly useful for military applications where immediate care upon the battlefield may otherwise not be available. Ointments could effectively cover irregular wound spaces whereas standalone hydrogel sheet dressings could cover more superficial wounds and infections. By covering wounds, hydrogels in accordance with the subject technology would not only reduce bacteria exposure but inhibit bacteria colonization as well. Another potential use is in the agriculture industry for time-dependent fertilization or pesticide application.

It will be appreciated by those of ordinary skill in the pertinent art that the functions of several elements may, in alternative embodiments, be carried out by fewer elements, or a single element. Similarly, in some embodiments, any functional element may perform fewer, or different, operations than those described with respect to the illustrated embodiment. Also, functional elements shown as distinct for purposes of illustration may be incorporated within other functional elements in a particular implementation. All patents, patent applications and other references disclosed herein are hereby expressly incorporated in their entireties by reference.

While the subject technology has been described with respect to preferred embodiments, those skilled in the art will readily appreciate that various changes and/or modifications can be made to the subject technology without departing from the spirit or scope of the invention as defined by the appended claims.

What is claimed is:

1. A hydrogel formulation comprising:
   a hydrogel having a particular mechanical strength;
   a salt composition for altering the mechanical strength; and
   a plurality of porous activated carbon powder nanoparticles comprising an adsorbed dosage of an antibiotic, said plurality of porous activated carbon nanoparticles embedded between a microporous structure of the hydrogel and said porous activated carbon nanoparticles facilitating the sustained release of the absorbed dosage of antibiotic.

2. The hydrogel formulation of claim 1, wherein the hydrogel is a Gellan film.

3. The hydrogel formulation of claim 1, wherein the dosage of absorbed antibiotic is vancomycin.

4. The hydrogel formulation of claim 1, further comprising a dosage of free antibiotic.

5. The hydrogel of claim 4, wherein the dosage of free antibiotic and the adsorbed dosage of antibiotic are both vancomycin.

6. The hydrogel of claim 1, wherein the porous activated carbon powder nanoparticles comprise micropores, mesopores, and macropores.

7. The hydrogel formulation of claim 1, further comprising a compound selected from the group consisting of an antibiotic, an antifungal compound, an anti-inflammatory compound, a proteins and enzymes to promote wound healing, hemostatic agents, diagnostic and contrast agents, extracellular matrix components, and combinations thereof.

8. A tunable antimicrobial-loaded hydrogel formulation comprising:
   a hydrogel having a pH level, wherein the hydrogel is a Gellan film;
   a salt composition in the hydrogel for setting the pH level;
   a first dosage of free antibiotic in the hydrogel; and
   a plurality of porous activated carbon powder nanoparticles in the hydrogel, the porous activated carbon powder nanoparticles facilitating a sustained release of a second dosage of antibiotic adsorbed in the activated carbon nanoparticles.

9. The hydrogel formulation of claim 8, wherein the dosage of absorbed antibiotic is vancomycin.

10. The hydrogel of claim 8, wherein the dosage of free antibiotic and the adsorbed dosage of antibiotic are both vancomycin.

11. The hydrogel of claim 8, wherein the porous activated carbon powder nanoparticles comprise micropores, mesopores, and macropores.

12. A method for treating burnt skin comprising the steps of:
   layering a hydrogel formulation directly upon the burnt skin, the hydrogel formulation comprising:
      a hydrogel having a particular mechanical strength;
      a salt composition for altering the mechanical strength; and
      a plurality of porous activated carbon powder nanoparticles comprising an adsorbed dosage of an antibiotic, said plurality of porous activated carbon powder nanoparticles embedded between a microporous structure of the hydrogel and said porous activated carbon powder nanoparticles facilitating the sustained release of the absorbed dosage of antibiotic.

13. The method of claim 12, wherein the hydrogel is a Gellan film.

14. The method of claim 12, wherein the dosage of absorbed antibiotic is vancomycin.

15. The method of claim 12, further comprising a dosage of free antibiotic.

16. The method of claim 15, wherein the dosage of free antibiotic and the adsorbed dosage of antibiotic are both vancomycin.

17. The method of claim 12, wherein the porous activated carbon powder nanoparticles comprise micropores, mesopores, and macropores.

18. The method of claim 12, further comprising a compound selected from the group consisting of an antibiotic, an antifungal compound, an anti-inflammatory compound, a proteins and enzymes to promote wound healing, hemostatic agents, diagnostic and contrast agents, extracellular matrix components, and combinations thereof.

* * * * *